US012746311B2

(12) United States Patent
Faltum

(10) Patent No.: US 12,746,311 B2
(45) Date of Patent: Sep. 29, 2026

(54) BREAST SHIELD AND BREAST SHIELD UNIT

(71) Applicant: MEDELA HOLDING AG, Baar (CH)

(72) Inventor: Carsten Faltum, Vitznau (CH)

(73) Assignee: MEDELA HOLDING AG, Baar (CH)

( * ) Notice: Subject to any disclaimer, the term of this patent is extended or adjusted under 35 U.S.C. 154(b) by 510 days.

(21) Appl. No.: 18/036,590

(22) PCT Filed: Dec. 13, 2021

(86) PCT No.: PCT/EP2021/085458
§ 371 (c)(1),
(2) Date: May 11, 2023

(87) PCT Pub. No.: WO2022/128899
PCT Pub. Date: Jun. 23, 2022

(65) Prior Publication Data

US 2024/0009360 A1 Jan. 11, 2024

(30) Foreign Application Priority Data

Dec. 15, 2020 (EP) .................................... 20214169

(51) Int. Cl.
*A61M 1/06* (2006.01)

(52) U.S. Cl.
CPC .................................. *A61M 1/064* (2014.02)

(58) Field of Classification Search
CPC ........ A61M 1/064; A61M 1/066; A61M 1/06; A61M 1/062
See application file for complete search history.

(56) References Cited

U.S. PATENT DOCUMENTS 4,799,922 A 1/1989 Beer et al.
8,118,772 B2 2/2012 Dao et al.
(Continued)

FOREIGN PATENT DOCUMENTS

CN 111886033 A 11/2020
WO WO-2018041365 A1 3/2018
(Continued)

OTHER PUBLICATIONS

International Search Report and Written Opinion of the International Searching Authority for International Application No. PCT/EP2021/085458, dated Mar. 28, 2022.
(Continued)

*Primary Examiner* — Jason E Flick
(74) *Attorney, Agent, or Firm* — MARSHALL, GERSTEIN & BORUN LLP

(57) ABSTRACT

A breast shield including a housing defining a nipple tunnel and adapted to receive a nipple, wherein the housing is provided with a milk port in communication with the nipple tunnel and a vacuum port in communication with the nipple tunnel. For allowing a tender accommodation of the human breast during the expression of milk the invention proposes an insert arranged within the housing and between the nipple tunnel and the milk port and/or the vacuum port. The breast shield unit for expressing human breast milk includes a unit housing with a receptacle adapted to detachably receive a breast shield, wherein the receptacle includes a vacuum interface for generating a negative pressure in the nipple tunnel and a milk interface leading to a milk container adapted to store the expressed human breast milk and wherein in an inserted stage, in which the breast shield is received within the receptacle, the vacuum port is in communication with the vacuum interface and the milk port is in communication with the milk interface.

13 Claims, 7 Drawing Sheets

(56) References Cited

U.S. PATENT DOCUMENTS

Figure 1:
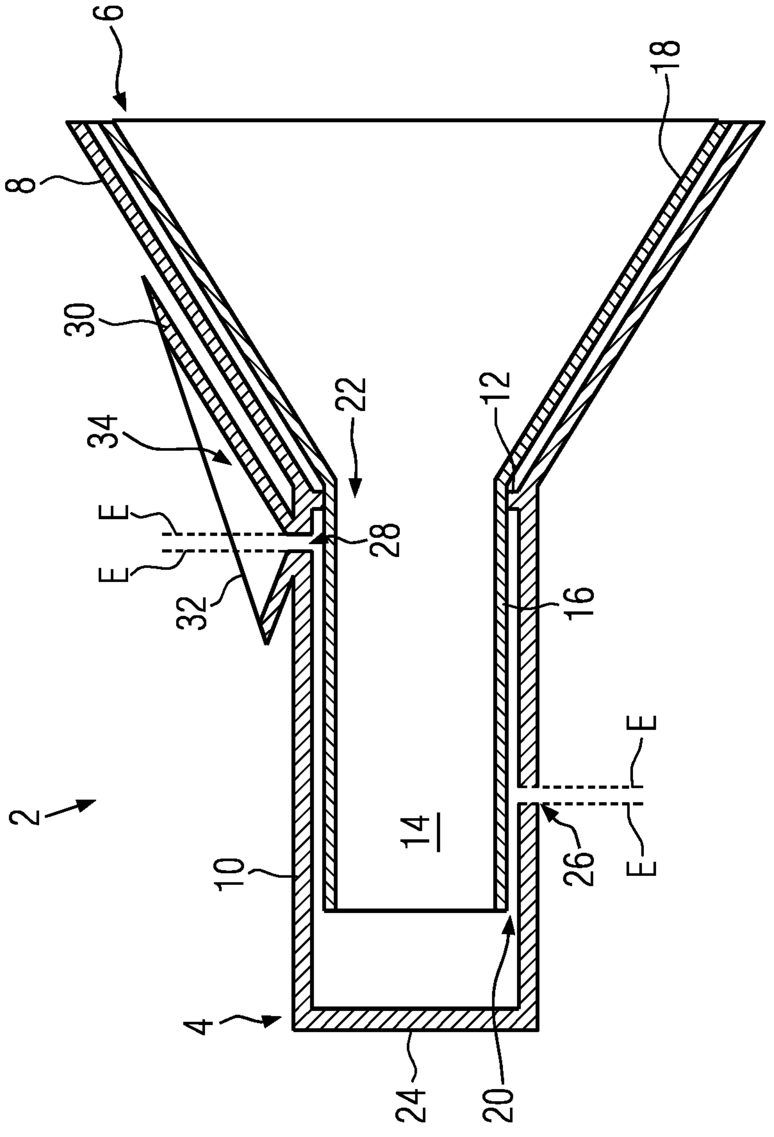

| | | | |
|---|---|---|---|
| 2004/0181187 A1 | 9/2004 | Warburton | |
| 2015/0217035 A1* | 8/2015 | Pollen | A61M 1/78 604/76 |
| 2015/0328380 A1 | 11/2015 | Furrer et al. | |
| 2018/0361040 A1* | 12/2018 | O'Toole | A61M 1/062 |
| 2021/0046227 A1 | 2/2021 | Bakker-Van Der Kamp et al. | |

FOREIGN PATENT DOCUMENTS

| | | |
|---|---|---|
| WO | WO-2018229504 | 6/2018 |
| WO | WO-2018229504 A1 | 12/2018 |

OTHER PUBLICATIONS

Extended Search Report for European Application No. 20214169.3, dated May 25, 2021.

Australian Examination Report No. 2 for Application No. 2021399798, dated Jun. 21, 2024.

Notification to Complete Formalities of Registration for Chinese Application No. 2021800842883, dated Aug. 3, 2026.

* cited by examiner

BREAST SHIELD AND BREAST SHIELD UNIT

CROSS-REFERENCE TO RELATED APPLICATION

This is the US national phase of International Patent Application No. PCT/EP2021/085458, filed Dec. 13, 2021, which claims priority to European Application No. 20214169.3, filed Dec. 15, 2020. The priority application, EP 20214169.3, is hereby incorporated by reference in its entirety.

The present invention relates to a breast shield comprising a housing defining a nipple tunnel and adapted to receive a nipple.

Such breast shield is known from WO 2018/229504 A1. The prior art breast shield has a housing defining a flange segment shaped to fit against a breast and a nipple tunnel segment surrounding the nipple tunnel. The breast shield according to this prior art has a milk port in communication with the nipple tunnel. Furthermore, a vacuum port is in communication with the nipple tunnel.

Due to this, a vacuum can be effective within the nipple tunnel in order to express human breast milk from the breast.

In the prior art mentioned above, the milk port is provided at a closed end section of the nipple tunnel. The vacuum port is provided on a circumference of the nipple tunnel.

The present invention aims to provide a breast shield allowing a tender accommodation of the human breast during the expression of milk.

As a solution to the above object, the present invention provides a breast shield as defined in claim 1. The inventive breast shield has a housing defining a nipple tunnel adapted to receive the nipple. As in the previously discussed prior art solution, a milk port and a vacuum port are provided, which are both in communication with the nipple tunnel. In the inventive solution, an insert is arranged within the housing and between the nipple tunnel and the milk port and/or the vacuum port. In other words, inner walls of the housing of the breast shield exhibiting the vacuum port and/or the milk port will not come into direct contact with the breast, in particular the nipple received within the nipple tunnel.

The insert may be arranged to fully or at least partially project above or beyond the milk port or the vacuum port. Such arrangement is in particular given if an axial extension of a bore defining the milk port or the vacuum port is aligned with material of the insert. Such axial extension of the bore may be fully or at least partially covered by material of the insert. As in prior art, the vacuum port and the milk port are in fluid communication with the nipple tunnel in order to generate a vacuum within the nipple tunnel, which vacuum will cause the expression of milk while allowing fluid flow of expressed mild from the nipple tunnel into the milk port.

Accordingly, a breast and in particular a nipple of the breast received within the breast shield will by no means be able to come into contact with the vacuum port or the milk port. While the breast shield of the present invention is usually composed of parts which are injection-molded and formed as unitary bodies, the bore defining the milk port and/or the vacuum port can have a constitution with could comprise obstacles or sharp edges leading to severe wounds on the sensitive nipple, which wounds by all means have to be avoided. Such effect is attained with the present invention by the insert arranged within the housing.

The insert of the present invention will provide smooth accommodation of the breast. For this, the housing may comprise a flange segment shaped to fit against the breast and a nipple tunnel segment defining the nipple tunnel. Alternatively, the housing may only provide the nipple tunnel segment defining the nipple tunnel. Such nipple tunnel segment may have a generally cylindrical constitution and/or may have a free open end section which abuts a shoulder defined by a unit housing of a breast shield unit. This shoulder will guarantee proper positioning of the housing within the unit housing. The shoulder is usually adapted to cooperate with the free open end section of the housing to avoid steps or sharp corners at the transition between the unit housing and the housing. In such a constitution, the breast may be accommodated in a receptacle provided by the unit housing, which receptacle may support a portion of the insert adapted to at least partially accommodate the breast.

Specifically, the present invention proposes a breast shield unit for expressing human breast milk comprising a unit housing with a receptacle adapted to detachably receive a breast shield, and further comprising a milk container adapted to store the expressed human breast milk, wherein the breast shield comprises a housing defining a nipple tunnel and adapted to receive a nipple, wherein the housing is provided with a milk port in communication with the nipple tunnel and a vacuum port in communication with the nipple tunnel, wherein the receptacle comprises a vacuum interface for generating a negative pressure in the nipple tunnel and a milk interface leading to the milk container, wherein in an inserted stage, in which the breast shield is received within the receptacle, the vacuum port is in communication with the vacuum interface and the milk port is in communication with the milk interface. This breast shield unit is characterized by an insert arranged within the housing and between the nipple tunnel and the milk port and/or the vacuum port.

According to a preferred embodiment of the present invention, the nipple tunnel has an open end section in communication with the flange segment of the housing and a closed end section opposite to the open end section. The nipple tunnel has a generally cylindrical constitution. Preferably, the longitudinal extension of the milk port and/or the longitudinal extension of the vacuum port extend in radial direction of the nipple tunnel. In other words, those ports are each or both provided on the circumferential surface defining the nipple tunnel.

According to a preferred embodiment of the present invention, the insert is formed by a unitary body comprising a nipple tunnel insert segment and a flange insert segment. The nipple tunnel insert segment is received within the nipple tunnel. The flange insert segment may be received within the flange segment of the housing and/or the receptacle of the unit housing. The insert may be constituted of the nipple tunnel insert segment and the flange insert segment, only. Ideally, the inner circumferential surface of the nipple tunnel insert segment and the flange insert segment are smooth, free of sharp edges or voids. The inner circumferential surface of the nipple tunnel insert segment merges into the inner circumferential surface of the flange insert segment smoothly and without steps. Preferably, the nipple tunnel insert segment is essentially of cylindrical form. The flange insert segment may assume a form which essentially corresponds to the shape of a cone in particular a frustocone. The cross section of the flange insert segment and the cross section of any part of the breast shield does not need to be round. It can also have a form which essentially and/or partially corresponds to the shape of a ball-shaped scraper in regard of the shape of a mothers breast.

The nipple tunnel insert may preferably be formed by a rather rigid material adapted to shield the milk port and/or the vacuum port from direct contact with the breast, in particular the nipple received within the nipple tunnel. The flange insert segment may be formed of a rather flexible material improving the woman's comfort feeling of the breast fitted against the breast shield or the unit housing and improving a vacuum-tight enclosure of the nipple received within the nipple tunnel. In such a case, the flange insert segment is supported by the flange segment and/or the receptacle, both being formed to provide full support of the breast, while not necessarily being in direct contact with the breast.

According to a preferred embodiment, the insert and/or the housing is formed as a unitary member. Such unitary member with portions of different flexibility may be made by co-injection-molding joining the flexible material with the hard material. The housing and/or the insert are usually made of plastic material. Preferably and in order to allow proper positioning and alignment of the breast within the breast shield, a substantially transparent material is used for forming the insert and/or the housing.

For improving cleaning, the insert is preferably detachably mounted to the housing. As in prior art, the housing is preferably detachably mounted to the unit housing. Thus, both elements of the breast shield, i.e. the housing and the insert can be dish-washed separately and may be replaced if need arises without the need to likewise replace the other of the insert and the housing.

In particular in case of an insert being detachably mounted to the housing, a sealing is arranged between the insert and the housing and/or the unit housing. This sealing or gasket is preferably arranged between an inner end of the flange segment or a conical in particular a frustoconical receptacle of the unit housing and the milk port and/or the vacuum port. For this preferred embodiment, it is assumed that the ports are each provided to circumferentially surround the nipple tunnel.

According to a further preferred embodiment of the present invention, there is provided a support section defining a diaphragm support adapted to detachably hold a diaphragm. This support section furthermore defines a pumping chamber, which pumping chamber is in communication with the vacuum port. The support section preferably is a unitary part of the housing. Respective support section preferably is arranged at an outer circumference of the nipple tunnel segment. In other words, a tube connecting the pumping chamber with the vacuum port extends radially from the nipple tunnel segment. However, the support may partially project over the flange segment of the housing. When being used, the breast shield will be detachably received within the above mentioned receptacle of the breast shield unit, specifically the unit housing thereof. This receptacle may be open to a diaphragm receptacle, which is adapted to receive the support section and the diaphragm to provide a further pumping chamber for the working fluid which drives the diaphragm in order to generate a generally cycling negative pressure within the nipple tunnel. The working fluid is accommodated within a path within the unit housing and between a source for negative pressure and the pumping chamber for the working fluid.

As the receptacle the diaphragm receptacle is usually defined by the unit housing of a breast shield unit. Such breast shield unit in any case will provide a vacuum interface for generating a negative pressure in the nipple tunnel. When being inserted into the receptacle, the vacuum port of the breast shield may be in direct fluid communication with this vacuum interface. Alternatively, the vacuum port may be in fluid communication with the pumping chamber for working fluid, which pumping chamber is closed by the diaphragm held by the housing.

The breast shield unit furthermore has a milk interface leading to a milk container adapted to store the expressed human breast milk. In an assembled state, in which the breast shield unit and the milk container are attached to the unit housing, the milk port is in fluid communication with the milk interface. Thus, expressed milk will leave the nipple tunnel through the milk port and enter into the milk interface thereby leading the milk to the milk container. It goes without saying that the milk interface and the milk port on the one hand and the vacuum interface and the vacuum port on the other are connected in a fluid-tight manner. For this, a gasket or seal preferably is provided between the milk port and the milk interface and the vacuum port and the vacuum interface, respectively. Such gasket or seal may be formed by soft elastomeric material defining the housing of the breast shield and/or the material at least partially forming the unit housing of the breast shield unit. The gasket or seal may be formed by a soft elastomeric material defining the diaphragm.

In an in-bra-embodiment, the unit housing usually receives and thereby accommodates a negative pressure source. This negative pressure source is usually provided by a pump, which is an electric pump.

The unit housing usually connects to the milk container, which milk container on a regular basis is detachably attached to the unit housing. As generally known from WO 2018/229504 A1, the milk container is preferably made of a transparent material.

The breast shield unit may also be configured as a wearable unit, in which the negative pressure source i.e. the pump is not integrated in the unit housing. Instead, the negative pressure may be generated in the breast shield via a tube connecting the breast shield with the negative pressure source.

The preferred embodiments of the inventive breast shield described herein may also be preferred embodiments of the breast shield unit defined above.

Figure 2:
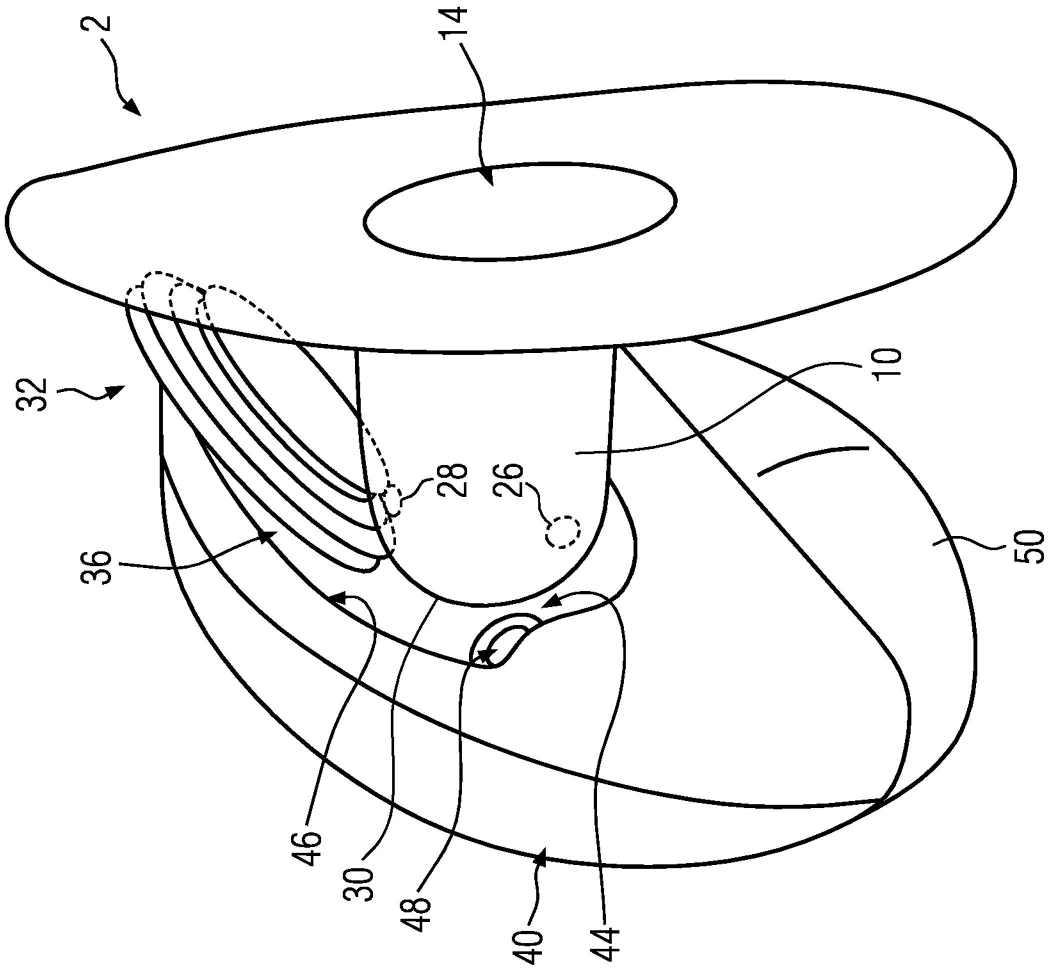
Figure 3:
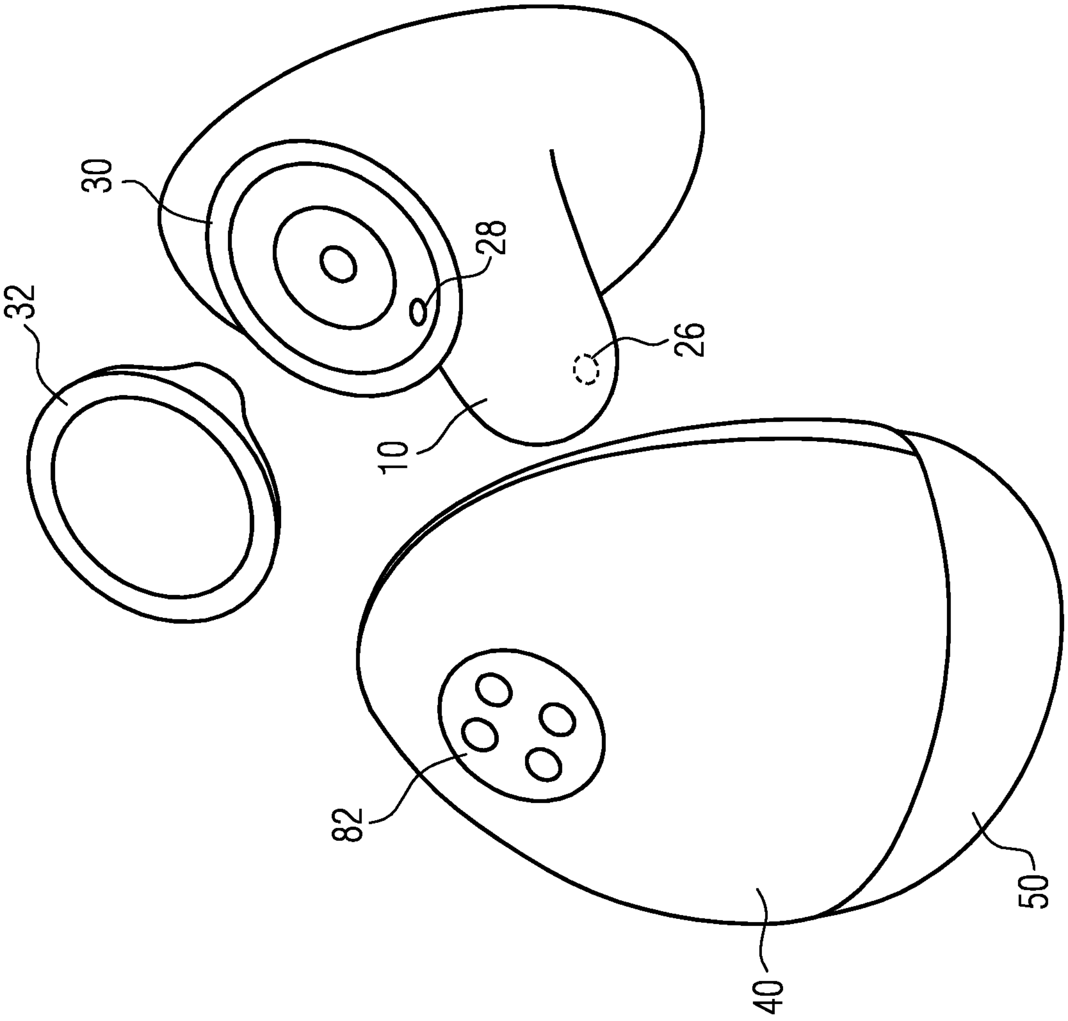
Figure 4:
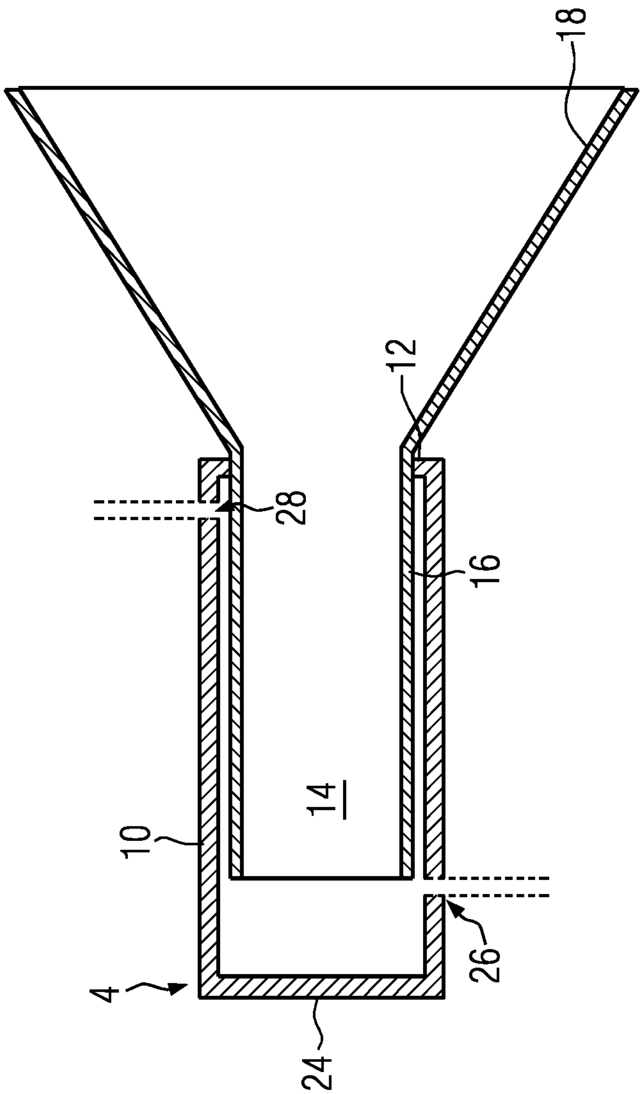
Figure 5:
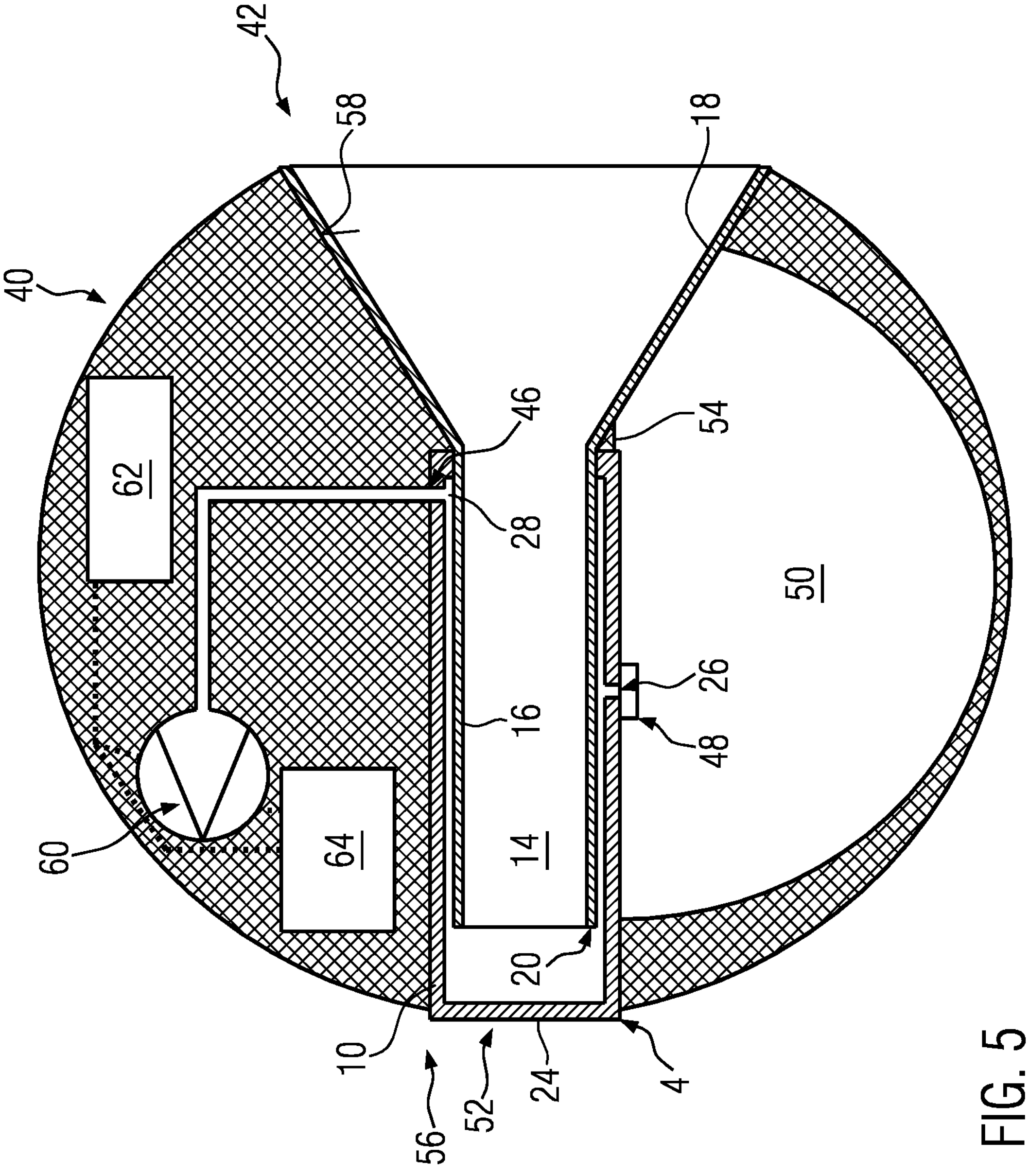
Figure 7:
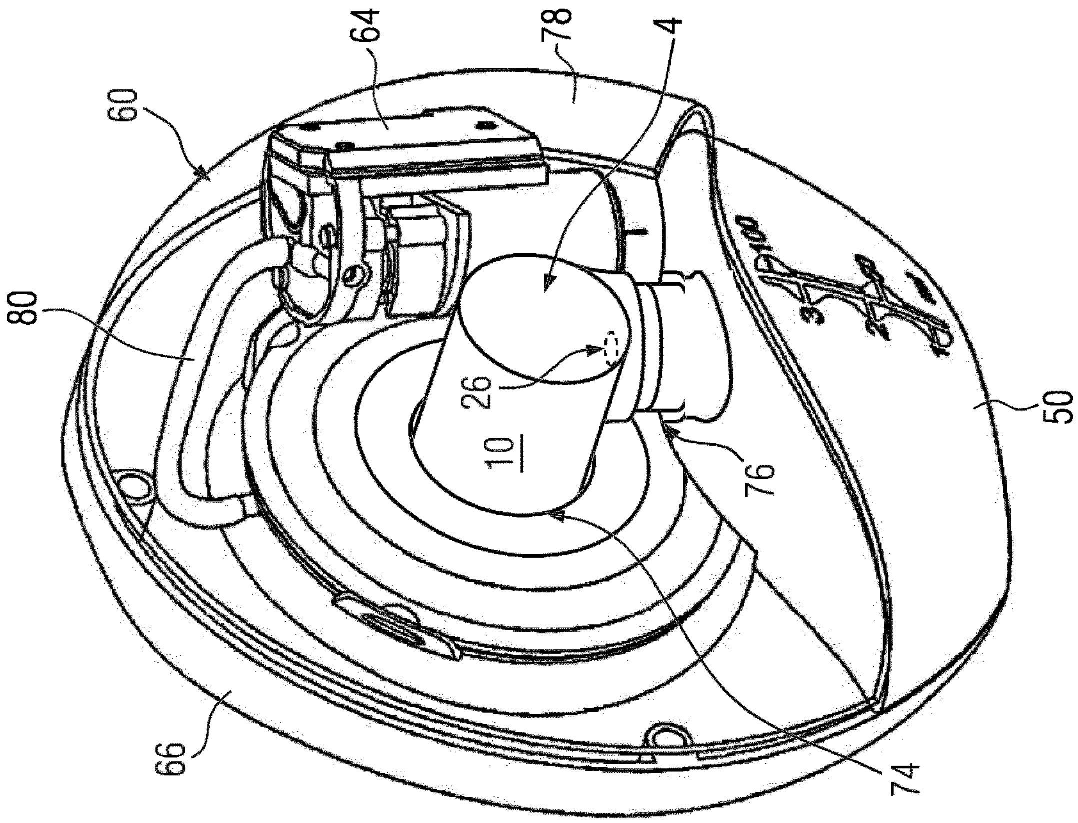
Figure 6:
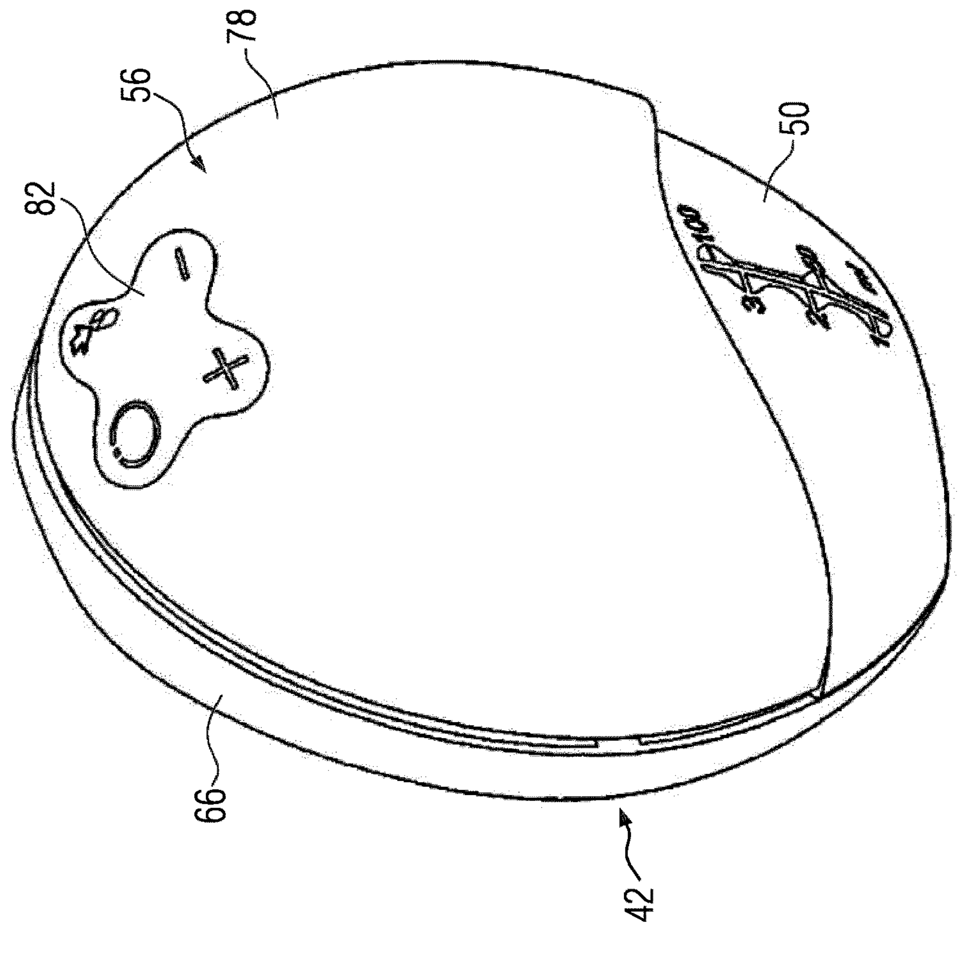
Figure 8:
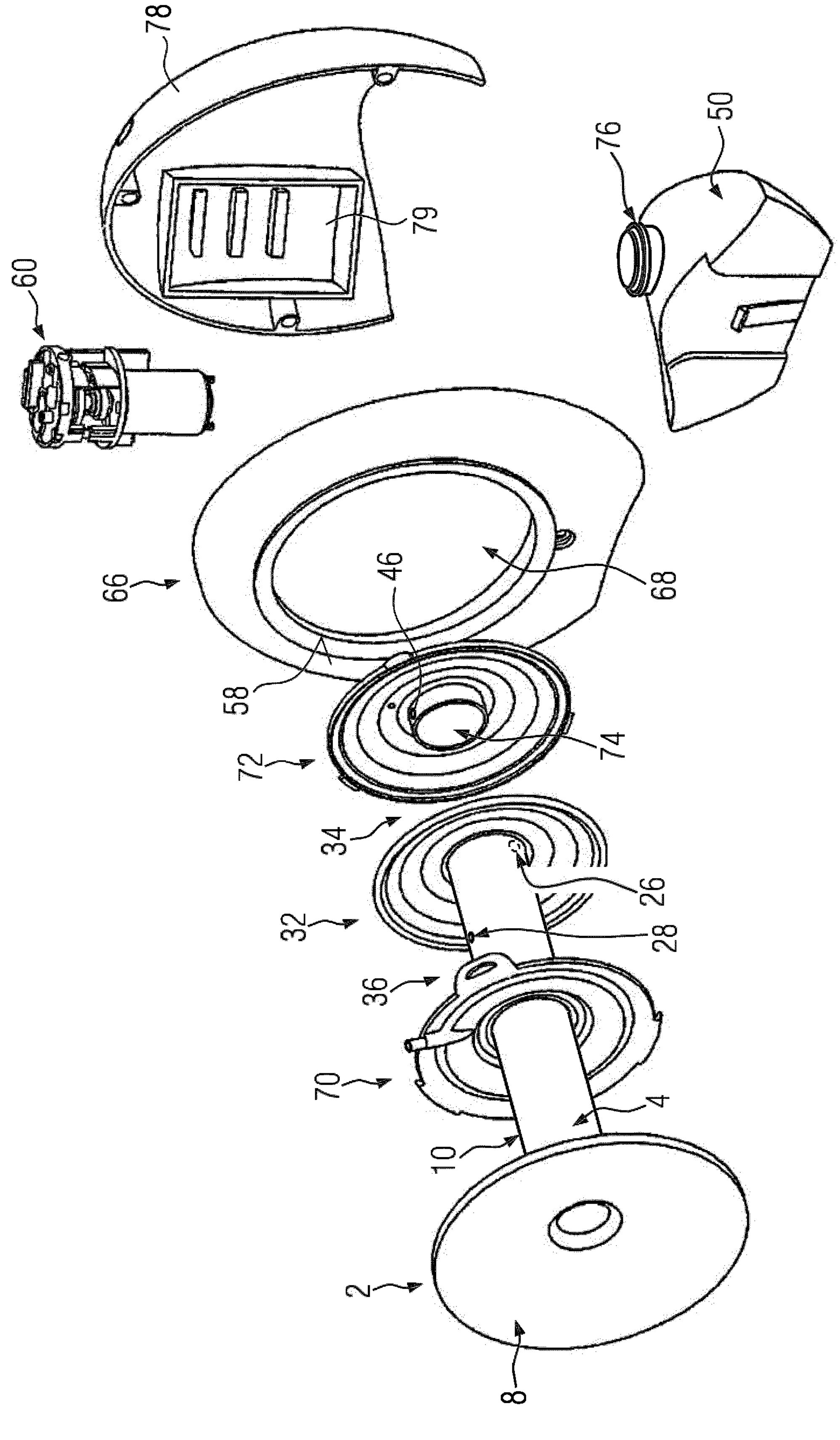

Further details and advantages of the present invention will become apparent from the following description of embodiments of the present invention in combination with the drawings. The drawings show FIG. 1 a longitudinal cross-sectional view of a first embodiment of a breast shield according to the present invention;

FIG. 2 a perspective exploded view of a breast shield unit of the present invention;

FIG. 3 a rear view of the breast shield unit according to FIG. 2;

FIG. 4 a longitudinal cross-sectional view according to FIG. 1 for an alternative embodiment of the breast shield FIG. 5 a schematic longitudinal cross-sectional view according of the embodiment according to FIG. 4 contained in a breast shield unit FIG. 6 a rear view of a further embodiment of a breast shield unit;

FIG. 7 the representation according to FIG. 6 with a partially removed unit housing shell and FIG. 8 an exploded perspective side view of the essential components of the breast shield unit according to FIGS. 6 and 7.

FIG. 1 shows examples of a breast shield 2 comprising a housing 4, which provides the outer portion of the breast shield 2 and an insert 6 received within the housing 4. The housing 4 has a flange segment 8 and a nipple tunnel segment 10. Between the transition of the flange segment 8 and the nipple segment 10, i.e. at an inner end of the flange segment 8, there is provided a gasket or sealing 12, which sealing 12 projects the inner circumferential surface defined by the nipple tunnel segment 10. The flange segment 8 is shaped to fit against a breast, whereas the nipple tunnel segment 10 is shaped to define a nipple tunnel 14.

Within the nipple tunnel 14 and between an inner circumferential surface defined by the nipple tunnel segment 10 and the nipple tunnel 14, there is provided a nipple tunnel insert segment 16, which forms part of the insert 6. The insert 6 furthermore has a flange insert segment 18 shaped to fit against the breast. Both segments 16, 18 are provided by a unitary body defining the insert 6. As derivable from FIG. 1, the insert 6 is received within the housing 4. An annular gap 20 is provided between the nipple tunnel insert 16 and the inner circumferential surface defined by the nipple tunnel segment 10. At an open end section 22 of the nipple tunnel 14, this annular gap 20 is sealed by the sealing 12. Between said sealing 12 and a closed end 24 of the nipple tunnel 14 i.e. the nipple tunnel segment 10, this nipple tunnel segment 10 projects over a milk port 26 and a vacuum port 28.

Those ports 26, 28 extend in radial direction of the nipple tunnel 14. As evident from FIG. 1, the nipple tunnel insert segment fully covers a longitudinal extension E of the milk port and the vacuum port, which longitudinal extension E is indicated in hashed lines. The longitudinal extensions E are the axial extension of walls defining a bores defining the milk port 26 and the vacuum port 28, respectively.

The nipple tunnel insert segment 16 is an essentially cylindrical member. The same applies to the nipple tunnel segment 10. The nipple tunnel insert segment 16 and the nipple tunnel 10 are usually arranged coaxially. As the ports 26, 28 are fully covered by the insert 6, the nipple will not come into direct contact with the rim of the bore defining the milk port 26 or the vacuum port 28. Thus, a wound on the sensitive nipple due to sharp edges e.g. made by drilling the port 26 or 28 can by all means be avoided.

The sealing 12 in the present embodiment is fixed to the housing 4. The insert 6 is releasably held within the housing 4. At a level of the sealing 12, the material forming the insert 6 is rather rigid to provide for a reliable seal between the insert 6 and the housing 4. In the present embodiment, the nipple tunnel insert segment 16 is made of a rigid plastic material in order to stabilize the annular gap 20 to allow movement of the sucked air through the vacuum port 28 and of the expressed milk 26 and through this annular gap 20.

The flange insert segment 18, however, may be formed of a rather flexible material to provide optimum comfort for the breast contacting the flange insert segment and for obtaining reliable vacuum-tight sealing between the inner circumferential surface of the flange insert segment 18 and the breast. The flange insert segment 18 can be supported by the flange segment 8 to assume a shape adapted to fit against the breast. Accordingly, and for the embodiment of FIG. 1, the flange segment 8 does not come into direct contact with the breast.

In FIG. 1, reference numeral 30 identifies a support section defining a diaphragm support adapted to detachably hold a diaphragm 32. This support section 30 defines a pumping chamber 34 between the diaphragm 32 and the vacuum port 28 for the air received in the nipple tunnel 14.

The embodiment of FIG. 1 can as such be inserted into a unit housing of a breast shield unit which will be discussed in further detail by referring to FIGS. 2 and 3. The housing 4 of the breast shield 2 may be secured to such unit housing frictionally and/or with a positive fit between the housing 4 and a unit housing 40. Specifically, the connection between the housing 4 and the unit housing 40 may be different than the frictional engagement between the insert 6 and the inner circumferential surface of the housing 4 of the breast shield 2. Nevertheless, the housing 4 as well as the insert 6 are preferably releasable from the unit housing of the breast shield unit.

On the front side directed to the human breast and identified with reference numeral 42, the unit housing 40 provides a receptacle 44 adapted to receive at least partially the breast shield 2 as specified above. The receptacle 44 is adapted to receive the nipple tunnel segment 10 of the housing 4. Respective receptacle 44 has a vacuum interface 46 and a milk interface 48. When the breast shield 2 is inserted into the receptacle 44, the milk interface 48 is in communication with the milk port 26. The unit housing 40 furthermore defines a vacuum interface 46 within a pumping chamber 36 for the working fluid, which pumping chamber is closed by the diaphragm 32. The diaphragm 32 is sealingly held against the surface of the unit housing.

In the embodiment of FIG. 1, the breast shield 2 as such has a housing 4 which is insertable into the receptacle 44. Further, the insert 6 as such can be inserted into the housing 4. The insert 6 is releasably received within the housing 4.

As further derivable from the enclosed Figure, the milk port 26 leads to a milk container 50. This milk container 50 may be provided with a seal which defines the milk interface 48. The milk container 50 is releasably coupled to the unit housing 40.

In the embodiment of FIG. 1, the housing 4 has a flange segment 8 which is shaped in order to fit against a breast. Direct contact between the breast and the breast shield 2 in this embodiment is made by the flange insert segment 18 of the insert 6. This flange insert segment 18 may be provided by a soft elastomeric material, which is held in shape and, thus, supported by the flange segment 8. The flange segment 8 in this embodiment is made of a rigid material.

In an alternative embodiment according to FIG. 4 the nipple tunnel insert segment 16 is slightly shorter than the insert segment 16 of FIG. 1. Thus, the insert only partially extends over the milk port 26. In other words, an open inner end of the nipple tunnel insert segment 16 lies within the hashed lines defining the longitudinal extension E of the milk port 26.

In this embodiment, the housing 4 is essentially reduced to the nipple tunnel segment 10. The forward open end 22 of the nipple tunnel 14 is provided with the sealing 12. As in the embodiment of FIG. 1, the opposite end 24 is closed.

In the embodiment of FIG. 5, the housing 4 is received within the unit housing 40. While the insert 6 is inserted into the unit housing 40 from the front side 42, the housing 4 is inserted from the other side. The housing 4 projects over the unit housing 40. This constitution gives additional length to the nipple tunnel 14. The sealing 12 is provided at the forward end of the housing 4. Both, the housing 4 and the insert 6 can be removed from the housing unit 40.

The unit housing 40 defines a housing receptacle 52, which is open from a rear side, which housing receptacle 52 terminates with a stop 54 formed by the unit housing 40. Level with this stop 54, the sealing 12 is provided at an inner circumference of the housing 4. As in the previously discussed embodiment of FIG. 1, the insert 6 is sealed against the housing 4 at this point. The insert 6 is inserted into the unit housing 40 from a side opposite to the insertion side of the housing 4.

As previously discussed, the flange insert segment 18 may be made of a soft elastomeric material, which in the embodiment of FIG. 5 is held in shape by a flange support surface 58 of the unit housing 40 defining the receptacle 44.

In the schematic representation according to FIG. 5, reference numeral 60 denotes a pump, which communicates with the vacuum interface 46. This pump 60 is energized by an accumulator 62 and controlled by a control 64, both being received within the unit housing 40.

FIGS. 6 through 8 show an alternative embodiment of a breast shield unit. Previously discussed elements, which have the same functionality and/or constitution as the previously discussed are identified with identical reference numbers. This embodiment is a variant of the embodiment discussed in WO 2013/010286, which is incorporated herein by reference.

The unit housing 40 of the respective embodiment has a unit housing ring 66, providing the flange support surface 58. The unit housing ring 66 defines an opening 68 which is larger than the outer diameter of the diaphragm 32 and first and second support elements 70, 72 encompassing the diaphragm 32 for defining the pumping chamber for the air 34 and the pumping chamber for the working fluid 36. The unit formed by joining the first and second support elements 70, 72 with the diaphragm 32 inter disposed may be releasably held within the unit housing 40. Respective unit has an inner opening 74 adapted to receive the housing 4.

In the embodiment of FIGS. 6 through 8, all elements of the previously discussed breast shield 2 are not shown in detail. The milk port 26 is provided at an outer circumference of the housing 4 near a free end i.e. the closed end section 24 of the nipple tunnel segment 10. In height direction, the vacuum port 28 is arranged opposite thereto and remote from the closed end section 24 of the nipple tunnel segment 10. In the assembled state, the vacuum port 28 is in communication with the vacuum interface 46 provided by a cylindrical segment of the second support element 72, whereas the milk port 26 sealingly abuts a milk valve 76 made of an elastomeric material, which milk valve 76 is releasably attached to the milk container 50 and corporates with the outer circumferential surface of the nipple tunnel segment 10.

As evident from FIGS. 6 and 7, the housing unit 40 comprises a unit housing shell 78, which includes a pump housing 79 and which is connected to the unit housing ring 66, which unit housing shell 78 covers and thereby accommodates the pump 60 and the control 64 realized as a sub unit within the unit housing 40. Between the pump 60 and the first support element 70, a tube 80 is shown which is sealingly connected to the pump 60 on one end and to the first support element 70 to form a path for the working fluid from the pump 60 to the pumping chamber 36. Finally, reference numeral 82 depicts a display.

LIST OF REFERENCE SIGNS

2 breast shield
4 housing
6 insert
8 flange segment
10 nipple tunnel segment
12 sealing
14 nipple tunnel
16 nipple tunnel insert segment
18 flange insert segment
20 annular gap
22 open end section
24 closed end section
26 milk port
28 vacuum port
30 support section
32 diaphragm
34 pumping chamber for the air
36 pumping chamber for the working fluid
40 unit housing
42 front side
44 receptacle
46 vacuum interface
48 milk interface
50 milk container
52 housing receptacle
54 stop
56 rear side
58 flange support surface
60 pump
62 accumulator
64 control
66 unit housing ring
68 opening
70 first support element
72 second support element
74 inner opening
76 milk valve
78 unit housing shell
79 pump housing
80 tube
82 display
E longitudinal extension

The invention claimed is:

1. A breast shield comprising a housing defining a nipple tunnel and adapted to receive a nipple, wherein the housing is provided with a milk port in communication with the nipple tunnel and a vacuum port in communication with the nipple tunnel, and an insert arranged within the housing and between the nipple tunnel and the milk port and/or the vacuum port, wherein a nipple tunnel segment of the housing and a nipple tunnel insert segment of the insert are arranged coaxially to provide an annular gap, which annular gap is sealed towards an open end of the nipple tunnel, which open end of the nipple tunnel is adapted to receive the nipple, and wherein of the annular gap is open opposite to the open end of the nipple tunnel.

2. The breast shield according to claim 1, the insert provided to at least partially extend over at a longitudinal extension (E) of the milk port and/or the vacuum port.

3. The breast shield according to claim 1, wherein at least one of the milk port or the vacuum port extends in radial direction of the nipple tunnel.

4. The breast shield according to claim 1, the nipple tunnel having an open end section and a closed end section opposite to the open end section.

5. The breast shield according to claim 1, the housing defining a flange segment shaped to fit against a breast and a nipple tunnel segment defining the nipple tunnel.

6. The breast shield according to claim 1, the insert being formed by a unitary body comprising a nipple tunnel insert segment received within the nipple tunnel and a flange insert segment shaped to fit against a breast.

7. The breast shield according to claim 1, wherein a substantially transparent material forming at least one of the insert or the housing.

8. The breast shield according to claim 1, wherein the insert is detachably mounted to the housing.

9. The breast shield according to claim 1 further comprising a sealing arranged between the insert and the housing.

10. The breast shield according to claim 1, the insert having a rigid section extending in circumferential direction, wherein the rigid section is provided at least one of between the nipple tunnel and the milk port or between the nipple tunnel and the vacuum port.

11. The breast shield according to claim 10, wherein at least a flange insert segment of the insert is received within a flange segment formed by the housing.

12. The breast shield according to claim 1, wherein a support section defining a diaphragm support adapted to detachably hold a diaphragm and to define a pumping chamber, wherein the pumping chamber is in communication with the vacuum port.

13. A breast shield unit for expressing human breast milk comprising a unit housing with a receptacle adapted to detachably receive a breast shield according to claim 1, wherein the receptacle comprises a vacuum interface for generating a negative pressure in the nipple tunnel and a milk interface leading to a milk container adapted to store the expressed human breast milk and wherein in an inserted stage, in which the breast shield is received within the receptacle, the vacuum port is in communication with the vacuum interface and the milk port is in communication with the milk interface.

* * * * *